Figure 1:
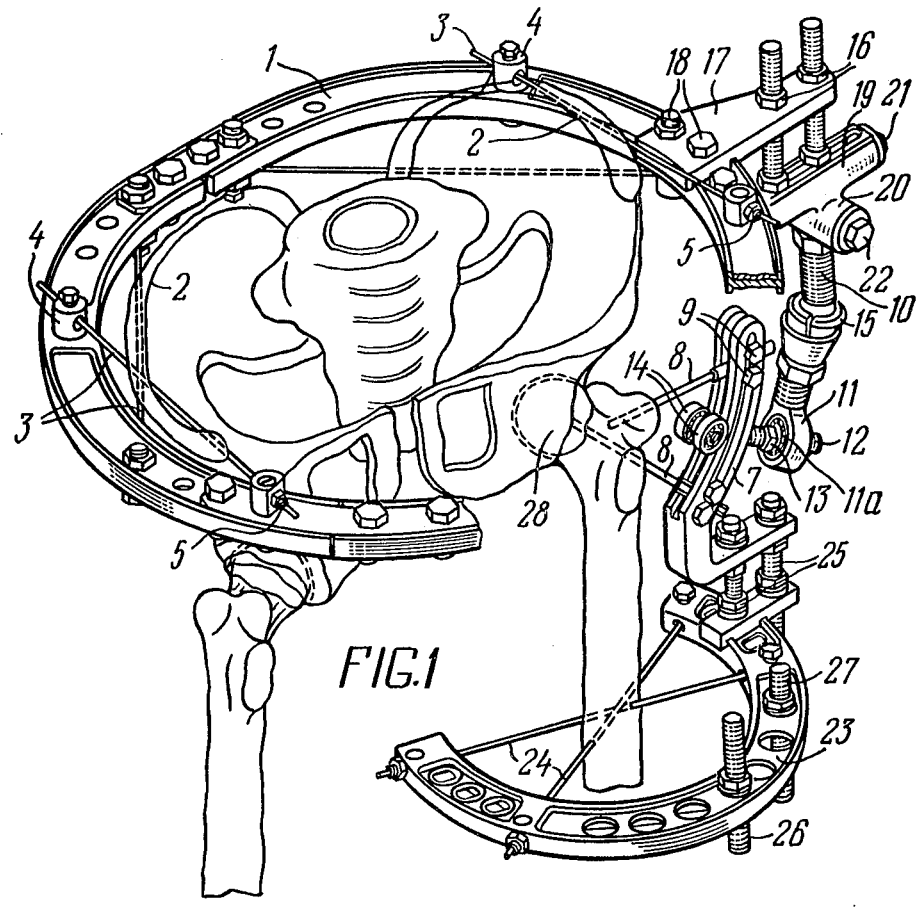

United States Patent [19]

Volkov et al.

[11] 4,185,623
[45] Jan. 29, 1980

[54] APPARATUS FOR RESTORATION OF HIP JOINT MOBILITY

[76] Inventors: Mstislav V. Volkov, 1 ulitsa Stroitelei, 6, korpus 1, kv. 63; Oganes V. Oganesian, ulitsa Pervomaiskaya, 74, kv. 87, both of Moscow, U.S.S.R.

[21] Appl. No.: 925,800

[22] Filed: Jul. 18, 1978

[51] Int. Cl.² ............................................. A61F 5/00
[52] U.S. Cl. .................................... 128/69; 128/82; 128/84 B; 128/92 A
[58] Field of Search ............... 128/82, 83, 84 R, 84 B, 128/84 C, 92 R, 92 A, 78, 75, 69

[56] References Cited

U.S. PATENT DOCUMENTS

| | | | |
|---|---|---|---|
| 3,976,061 | 8/1976 | Volkov et al. | 128/92 A X |
| 3,993,055 | 11/1976 | Volkov et al. | 128/84 B |
| 4,006,740 | 2/1977 | Volkov et al. | 128/84 B |

*Primary Examiner*—Ronald L. Frinks
*Attorney, Agent, or Firm*—Steinberg & Blake

[57] ABSTRACT

A pelvic yoke of an apparatus is secured on the upper flaring portion of the ilium by means of traction wires. A distractor with provision for adjusting movements in two mutually perpendicular planes, the frontal and the sagittal, is connected with said yoke and is fastened through a hinged joint on the thigh bone. The hinged joint is formed by rollers, disposed on an arc-like guide, situated in the frontal plane and fastened to the greater trochanter of the thigh bone. The hinged joint comprises also a spherical locking joint, fastened on the distractor. Such an apparatus provides for the complete relief of a hip joint during its healing while preserving its functions.

5 Claims, 2 Drawing Figures

APPARATUS FOR RESTORATION OF HIP JOINT MOBILITY

This invention relates to medical equipment and more particularly to an apparatus for the restoration of hip joint mobility.

Known in the art are mechanical-therapeutic apparatus used for the restoration of the mobility of the hip joint. However, these known apparatus fail to provide for simultaneous relief of the hip joint and exercise in the relieved joint with constant preset distraction between the articular ends, removing the harmful reciprocal pressure and friction of the articular ends, leading to a destructive effect on the articular surfaces. Attempts to use for the restoration of hip joint mobility prior art apparatus intended for the dynamic relief of the elbow joint, the wrist joint, the knee joint and the ankle joint did not produce the desired effect and proved unsuitable.

It is an object of the present invention to provide an apparatus for the restoration of the mobility of the hip joint, simultaneously providing for the relief and exercise of same.

This object is achieved by that an apparatus for the restoration of the mobility of the hip joint, according to the invention, comprises a pelvic yoke with traction wires for securing in the upper flaring portion of the ilium, a distractor embodied with the possibility of adjustment movements in two mutually perpendicular planes, frontal and sagittal, and a hinged joint for securing said distractor on the thigh bone.

An advantage of the proposed apparatus is that it provides the possibility of preserving, by adjustment movements, a constant preset clearance between the articular ends, which excludes harmful mutual pressure and friction of the articular surfaces. Simultaneously ensured is the gradual and dosed restoration of the anatomy and functions of the joint in a short period of time.

It is preferable that the hinged joint be embodied with the utilization of rollers disposed in an arc-like guide, situated in the frontal plane and connected to the greater trochanter of the thigh bone, and a spherical locking joint connected to said rollers, secured on the distractor and having an axis of rotation coincident with the frontal axis of rotation of the hip joint.

In order to ensure the possibility of adjusting the position of the distractor, a means is provided embodied as mutually perpendicular casings with slots, in which screw pairs connected with the distractor are movably disposed.

Another embodiment has a spherical joint connected with the rollers by means of a stirrup and a screw pair.

For effecting passive measured movement in the hip joint an additional yoke is provided, secured on the thigh bone.

Figure 2:
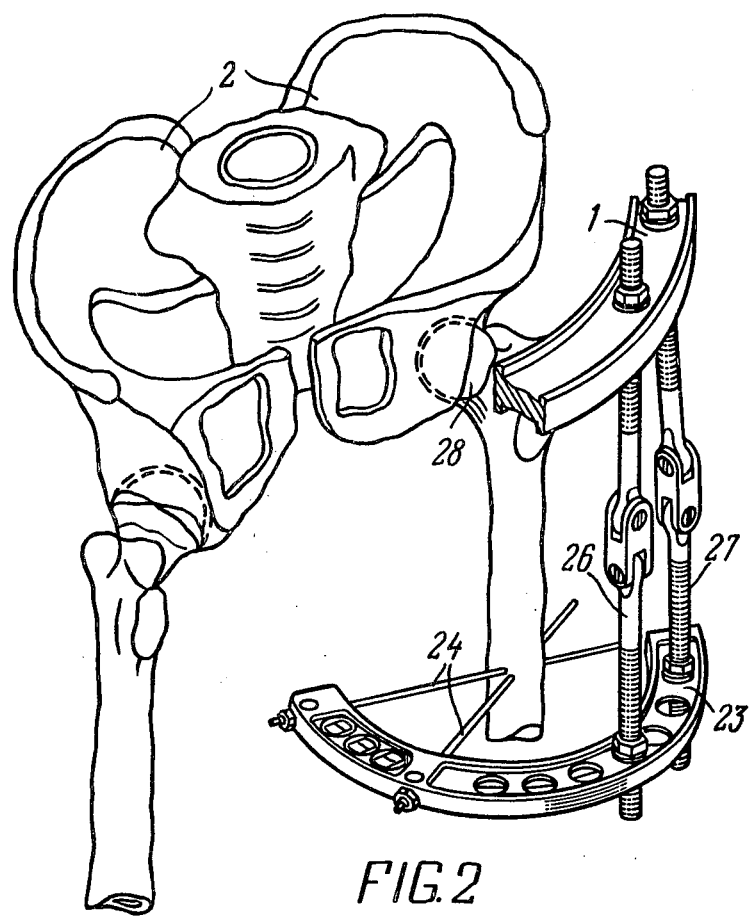

The invention will now be described in greater detail with reference to a concrete embodiment thereof, taken in conjunction with the accompanying drawings, wherein:

FIG. 1 shows an apparatus for the restoration of hip joint mobility, according to the invention;

FIG. 2 demonstrates the connection of the pelvic yoke with the flexion-extension device.

Referring now to FIG. 1, which shows the proposed apparatus for the restoration of the mobility of the hip joint, it can be seen that a sectional pelvic yoke 1 (shown in the Figure in part) secured on the iliac bones 2 of the patient by means of traction wires 3, passed through said bones. Such a yoke is well known to those skilled in the art and must be made of some strong material, for example, titanium. The traction wires 3 are fastened by wire holders 4, for example, in the form of bushes with holes, through which the wires are passed. It is advisable to ensure the possibility of adjusting the tension of the wires, for which they are provided with a thread at the ends and nuts 5, screwed onto the threaded portions of the traction wires.

An extensible distractor 10 of the apparatus has at one end a stirrup 11 with a bearing 11a fastened thereon, and secured on a screw 12 by means of locking nuts 13. Fastened at the other end of the axial screw 12 are rollers 14, which move along the inner concave surface of the arc-like guide 7.

The arc-like guide 7 is secured on the proximal end of the thigh bone by means of nails 8. The nails 8 are secured between two plates of the arc-like guide with the aid of coupling bolts 9.

A special nut (not shown in the Figure) serves for fixing the position of the rollers in the guide 7. The extensible distractor has a spherical locking joint 15 situated above the bearing 11a, intended for drawing and fastening the end of the distractor together with the bearing 11a to the frontal axis of rotation of the joint hip. The other end of the distractor is fastened by means of adjusting nuts 16 to a plate 17, secured with the aid of bolts 18 to the pelvic yoke 1. The distractor is provided with two mutually perpendicular guiding cylinders 19 and 20. Moving in each cylinder 19 and 20 by means of a motion screw is a guide nut (not shown in the Figure) with the end of the extensible distractor fastened in it, which results in the movement of the pelvic yoke 1 relative to the arc-like guide 7. Upon the rotation of the motion screw 21 of the cylinder 19 the pelvic yoke and the guide move in the frontal plane. By rotating the motion screw 22 of the cylinder 20 the pelvic yoke is moved relative to the arc-like guide in the sagittal plane.

A thigh yoke 23 by means of two traction wires 24 secures the diaphysis of the thigh bone. It is connected with the arc-like guide 7 by means of two screws 25.

A flexion-extension device 26 (FIG. 2) connects the thigh yoke with the pelvic yoke. An adducting-abducting device 27 connects the outer branch of the thigh yoke with the pelvic yoke. The flexion-extension device and the adducting-abducting device have two mutually perpendicular uniaxial joints, which provide the possibility for flexing and extending, and also for adducting and abducting the thigh.

The proposed apparatus is applied to a patient in the following way.

At first, the traction wires 3 are drawn through the upper flaring portion of the ilium on both sides and under an angle to one another. The ends of the wires are tightened up and secured in the yoke. After the pelvic yoke has been applied, the application of the arc-like guide 7 is started. Two nails 8 are drawn into the proximal end of the thigh bone at an angle of 50-80° to one another, their outer ends being fixed in the arc-like guide 7 so that the centre of the circumference of the guide 7 coincides with that of the head of the thigh bone 28.

Then, the application of the distractor 10 is begun, with the proximal end fixed to the pelvic yoke, and the distal, to the frontal axial hinge 12 which ends in a bearing.

If the apparatus is being applied with the purpose of releaving the joint and for active movement in the joint released by the apparatus, then with this the application of the proposed apparatus is completed.

If, in addition to relieving the hip joint, it is necessary to carry out passive measured movement in it, then the thigh yoke 23 is applied as well as the flexion-extension device 26 and the adducting-abducting device 27.

After the application of the apparatus, the required slit width between the articular ends is ensured by means of the nuts 13 of the screw 12.

By rotating the outer nut with the inner nut released, the axial screw is moved relative to the bearing in the external direction, which results in distraction of the articular ends of the hip joint. After establishing the preset width of the clearance between the head of the thigh bone 28 and the cotyloid cavity, the nuts 13 are tightened up on the bearing.

The reposition of articular ends in the apparatus is carried out in the following way. In order to preclude the lengthwise displacement of the articular ends, the adjustment nuts 16 of the distractor are rotated. Widthwise, shifts are removed by rotating the screws 21 and 22 of the guiding cylinders 19 and 20 of the apparatus. For removing flexion or extension contracture and exercising the flexion-extension movements in the apparatus the flexion-extension device 26 is mounted thereto. For removing adducting or abducting contracture and exercising adducting-abducting movements the adducting-abducting device 27 is mounted on the apparatus.

The utilization of the proposed invention provides for complete relief of the hip joint during its healing while preserving its function and facilitating the restoration of the anatomy and function of the joint in a brief period of time. The closed gradual and dosed setting of a dislocated hip bone by means of the proposed apparatus, followed by measured exercising movements in the joint and the restoration of its functions makes it unnecessary for the patient to undergo open surgery and is much more physiological than other methods of treating the hip joint.

What is claimed is:

1. An apparatus for the restoration of hip joint mobility, comprising a pelvic yoke intended for being secured in the upper flaring portion of the ilium, traction wires for securing said yoke in said upper flaring portion of the ilium, a distractor connected with said pelvic yoke, a means for adjustable movements of said distractor in two mutually perpendicular, frontal and sagittal planes, a hinged joint for securing said distractor on a thigh bone.

2. An apparatus as claimed in claim 1, in which the hinged joint is formed by rollers disposed in an arc-like guide situated in the frontal plane and adapted to be affixed to the greater trochanter of the thigh bone and connected to said rollers by means of a spherical locking joint, secured on the distractor and having an axis of rotation coincident with the frontal axis of rotation of the hip joint.

3. An apparatus as claimed in claim 1, comprising a device for adjusting the distractor and hinged joint, embodied in the form of mutually perpendicular casings with slots in which screw pairs connected with the distractor are disposed.

4. An apparatus as claimed in claim 2, comprising a spherical joint connected with the rollers by means of a stirrup and a screw pair.

5. An apparatus as claimed in claim 1, characterized in that it has an additional thigh yoke to be secured on the thigh bone and connected through a flexion-extension device with said pelvic yoke.

* * * * *